US00PP31363P2

(12) United States Plant Patent

Bron et al.

(10) Patent No.: US PP31,363 P2
(45) Date of Patent: Jan. 14, 2020

(54) *MISCANTHUS* PLANT NAMED 'EMPMIS02'

(50) Latin Name: *Miscanthus sinensis*
Varietal Denomination: EMPMIS02

(71) Applicants: Hogendoorn Holland B.V., Wijk en Aalburg (NL); Empho B.V., Beritsum (NL)

(72) Inventors: Piet Bron, Beritsum (NL); Elbert van Vulpen, Wijk en Aalburg (NL)

(73) Assignee: PI RO NEW PLANTS, Sloten (NL)

( * ) Notice: Subject to any disclaimer, the term of this patent is extended or adjusted under 35 U.S.C. 154(b) by 0 days.

(21) Appl. No.: 15/998,018

(22) Filed: Jun. 12, 2018

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
CPC ... A01H 5/12; A01H 5/02; A01H 5/00; A01H 5/10; A01H 6/46; A01H 6/00
See application file for complete search history.

(56) References Cited

PUBLICATIONS

Floral Daily. Part 1 Novelties at Plantarium 2017, retrieved on Apr. 29, 2019, retrieved from the Internet at https://www.floraldaily.com/article/9010517/novelties-at-plantarium-2017/, pp. 1,16,24. (Year: 2017).*

* cited by examiner

*Primary Examiner* — June Hwu
(74) *Attorney, Agent, or Firm* — Penny J. Aguirre

(57) ABSTRACT

A new cultivar of *Miscanthus, Miscanthus sinensis* 'EMPMIS02', that is characterized by its flower plumes that are pink in color, its compact plant habit and short plant height, its long flowering period, and its floriferous blooming habit in producing numerous flowering stems.

2 Drawing Sheets

Botanical classification: *Miscanthus sinensis.*
Cultivar designation: 'EMPMIS02'.

CROSS REFERENCE TO A RELATED APPLICATION

This application is related to a European plant breeders' rights application filed on Jan. 29, 2017, application No. 2017/0249. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Miscanthus sinensis* and will be referred to hereafter by its cultivar name, 'EMPMIS02'. 'EMPMIS02' represents a new cultivar of Japanese silver grass, a cold hardy, perennial ornamental grass grown for landscape use.

'EMPMIS02' was discovered by the Inventors as a chance seedling in a trial field plot in Berltsum, The Netherlands in August of 2010. The parentage is unknown.

Asexual propagation of the new cultivar was first accomplished by division by one of the Inventors in Jan. 2015in Harich, The Netherlands. Asexual propagation by division has determined that the characteristics of the new cultivar are stable and are reproduced true to type in successive generations.

STATEMENT DESIGNATING A GRACE PERIOD UNDER 1209(b)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventors.

SUMMARY OF THE INVENTION

The following traits have been repeatedly observed and are determined to be the characteristics of the new cultivar. These attributes in combination distinguish 'EMPMIS02' as a unique cultivar of *Miscanthus.*

1. 'EMPMIS02' exhibits flower plumes that are pink in color.
2. 'EMPMIS02' exhibits a compact plant habit and short plant height.
3. 'EMPMIS02' exhibits a long flowering period.
4. 'EMPMIS02' exhibits a floriferous blooming habit in producing numerous flowering stems.

'EMPMIS02' can be most closely compared to the cultivar 'Kleine Fontaine' (not patented) and 'EMPMIS01' (U.S. Plant Pat. No. 30,802). 'Kleine Fontaine' is similar to 'EMPMIS02' in having weeping inflorescences. 'Kleine Fontaine' differs from 'EMPMIS02' in having a taller plant height, flowers that are light red in color, and in having a shorter blooming period by commencing bloom later in the season (August). 'EMPMIS01' is similar to 'EMPMIS02' in plant height. 'EMPMIS01' differs from 'EMPMIS02' in having flowers plumes that are red in color.

BRIEF DESCRIPTION OF THE DRAWINGS

The accompanying colored photographs illustrate the overall appearance and distinct characteristics of the new *Miscanthus*. The photographs were taken in September of plants 4 years in age as grown outdoors in a 40-cm container in Berltsum, The Netherlands.

The photograph in FIG. 1. provides a side view of a plant of 'EMPMIS02' and illustrates the overall plant habit and general appearance in bloom.

Figure 1:
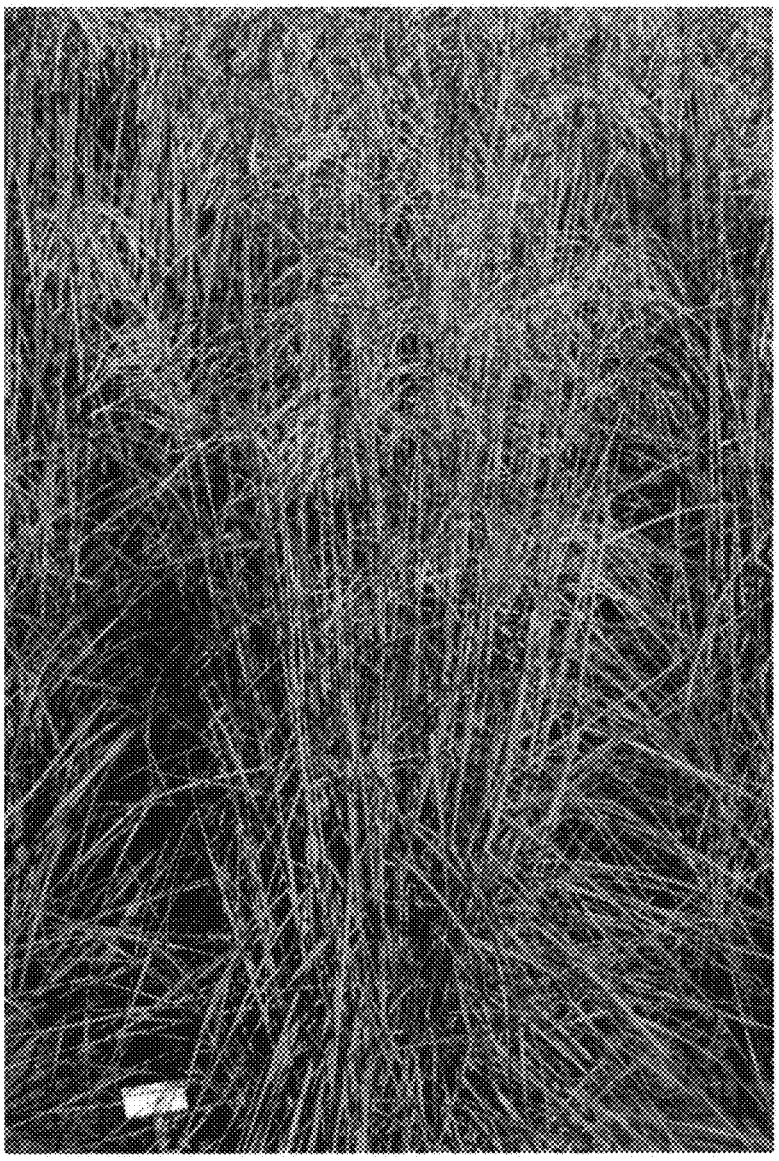
Figure 2:
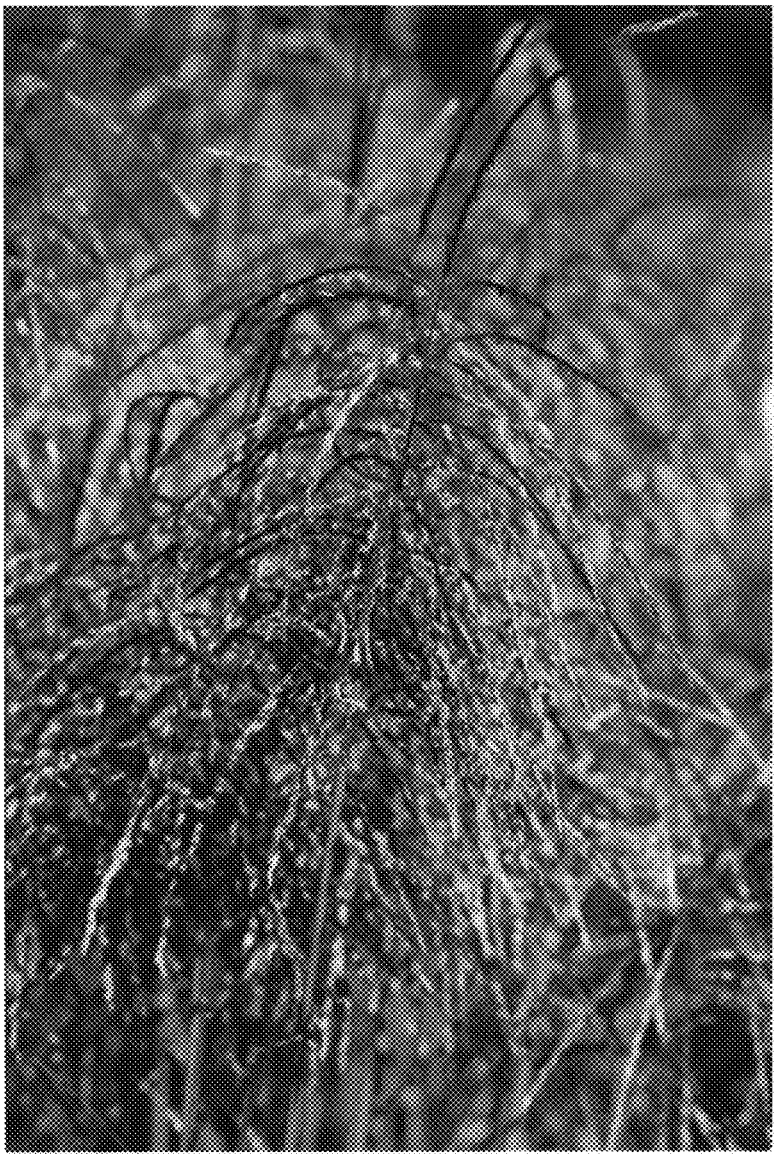

The photograph in FIG. 2. provides a close-up view of the inflorescences of 'EMPMIS02'.

The colors in the photographs are as close as possible with the photographic and printing technology utilized and the color values cited in the Detailed Botanical Description accurately describe the colors of the new *Miscanthus*.

DETAILED BOTANICAL DESCRIPTION

The following is a detailed description of 3-year-old plants of the new cultivar as grown outdoors in in a trail plot in Berltsum, The Netherlands. The phenotype of the new cultivar may vary with variations in environmental, climatic, and cultural conditions, as it has not been tested under all possible environmental conditions. The color determination is in accordance with The 2015Colour Chart of The Royal Horticultural Society, London, England, except where general color terms of ordinary dictionary significance are used.

General description:

*Blooming period.*—Blooms in July through early October in The Netherlands.

*Plant type.*—Herbaceous perennial.

*Plant habit.*—Clump-forming, ornamental grass with an upright, broad form and dense, compact bushy foliage.

*Height and spread.*—Average of 1 m in height and 100 cm in diameter (30 cm at base) as a 3-year-old plant in the landscape.

*Hardiness.*—At least in U.S.D.A. Zones 6 to 10.

*Diseases and pests.*—No susceptibility or resistance to disease or pests has been observed.

*Root description.*—Thin fleshy, NN155D flushed with 181B and N34B with root tips 2D.

*Root development.*—An average of 4 months for root development in a liner from a division and an average of 6 months to produce a young rooted plant.

*Propagation.*—Division.

*Growth rate.*—Moderately vigorous.

Culm (stem) description:

*General.*—Rounded, strong, unbranched.

*Culm aspect.*—Growing from the base, held upright, vertically.

*Culm quantity.*—Average of 130 basal shoots.

*Culm color.*—Young 144C, mature internodes 151B and slightly flushed with 59D, mature nodes 152C and becoming flushed with 175A.

*Culm size.*—Up to 1 m in length, average of 3.5 mm in diameter with nodes 3.8 mm in diameter.

*Culm internode length.*—5 mm to 10 cm.

*Culm surface.*—Glabrous with nodes hairy with hairs up to 2.5 mm in length.

*Culm pith.*—NN155C in color.

Foliage description:

*Leaf shape.*—Linear.

*Leaf division.*—Simple.

*Leaf base.*—Sheathed.

*Leaf apex.*—Very long acuminate.

*Leaf aspect.*—Held 30° to 40° upward from sheath, slightly cascading.

*Leaf venation.*—Parallel, only mid-vein is visible.

*Leaf margins.*—Entire, with sharp short upwards bristles that are not visually noticeable.

*Leaf size.*—Blade; to 60 cm in length and 9 mm in width, sheath; up to 20 cm in length 1 cm in diameter.

*Leaf surface.*—Blade; upper and lower surface glabrous with upper surface slightly glaucous when mature, sheath; glabrous and smooth.

*Leaf ligules.*—Semi-circular in shape, membranous with hairy margin, 1 mm in width, 165C in color.

*Leaf number.*—An average of 10 per culm.

*Leaf arrangement.*—Alternate.

*Leaf color.*—Blades; young upper surface; 144B with mid-vein 157D, young lower surface 138A with mid-vein 143C, mature upper surface 146B with mid-vein 157D, mature lower surface 137C with mid-vein 137D, sheaths; outer surface 144D flushed with 59A and small dots of 33A, inner surface 144D with very faint flush of 59A, both surfaces after a hard frost in fall turn to primarily 161C.

Flower description:

*General description.*—Compact, fan-shaped panicle terminating from each stem, composed of numerous slender, silky aggregate cascading racemes of spikelets.

*Lastingness of inflorescence.*—Average of 1 month for spikelets to drop, rest of raceme persistent into winter.

*Fragrance.*—None.

*Panicle size.*—Up to 20 cm in length and width.

*Panicle color.*—A blend of 60C, 64C, and N155D.

*Flower number.*—An average of 400 flowers per inflorescence.

*Flower buds.*—An average of 6 mm in length, 1.5 mm in diameter, narrow ovate in shape, 60C in color, surface is smooth, glabrous, moderately glossy and covered with fine hairs extending from the base of the floret.

*Axis* (*Rachis*).—5 to 16 cm in length and 0.6 mm in width, moderately strong, surface smooth and moderately glossy and 144C in color with tint of 61A.

*Peduncle.*—An average of 2 mm in length and 0.6 mm in width on longer one and up to 1 mm and 0.6 mm in width on shorter one, moderately strong, smooth and glabrous, moderately glossy and 144C in color with tint of 61A.

*Pedicels.*—None, single flowers on peduncle.

*Spikelet description* (*flowers*).—2 flowers per spikelet, an average of 1.5 cm in length (including callus hairs) and 4 mm in width, consisting of 2 glumes, 1 palea, 1 lemma, surface slightly glossy, ovate in shape, strongly concave, base cuneate, no venation visible, not fading, 2 glumes oppositely placed at the base of each individual flower, lemma and palea oppositely placed above the glumes, margins of glumes and lemma entire, margins of palea fringed, apex of glumes and palea acuminate, apex of lemma narrow acute with awn: 4 mm in length and 144C tinted with 61A in color, glumes an average of 3 mm in length and 0.7 mm in width, lemma an average of 4 mm in length and 0.5 mm in width, palea 4 mm in length and 0.7 mm in width, color; when opening both surfaces of glumes 162D with veins N155B, lemma and palea 58D, one whorl of fine callus hairs extending from the base of the floret; 1 to 4.5 mm in length, 62C in color, overall spikelet color: a blend of 62D, N155B and 58D, overall flower color in fall after a hard frost turn to a blend of 183D and 164C.

Reproductive organs:

*Androecium.*—Stamens; average of 3, anthers; short oblong in shape, 1.8 mm in length, 0.5 mm in width, 59B in color, filament; filiform, average of 2 mm in length, transparent and N155D in color, pollen; minimal in quantity and 85D in color.

*Gynoecium.*—Pistil; 2, 3.5 mm in length, stigmas; plumose, 0.2 mm in length, 59A in color, style; 1 mm in length, NN155D in color, ovary; 144A to 144B in color.

*Caryopsis.*—No caryopsis production has been observed to date.

It is claimed:

1. A new and distinct cultivar of *Miscanthus* plant named 'EMPMIS02' as herein illustrated and described.

* * * * *